Figure 1:
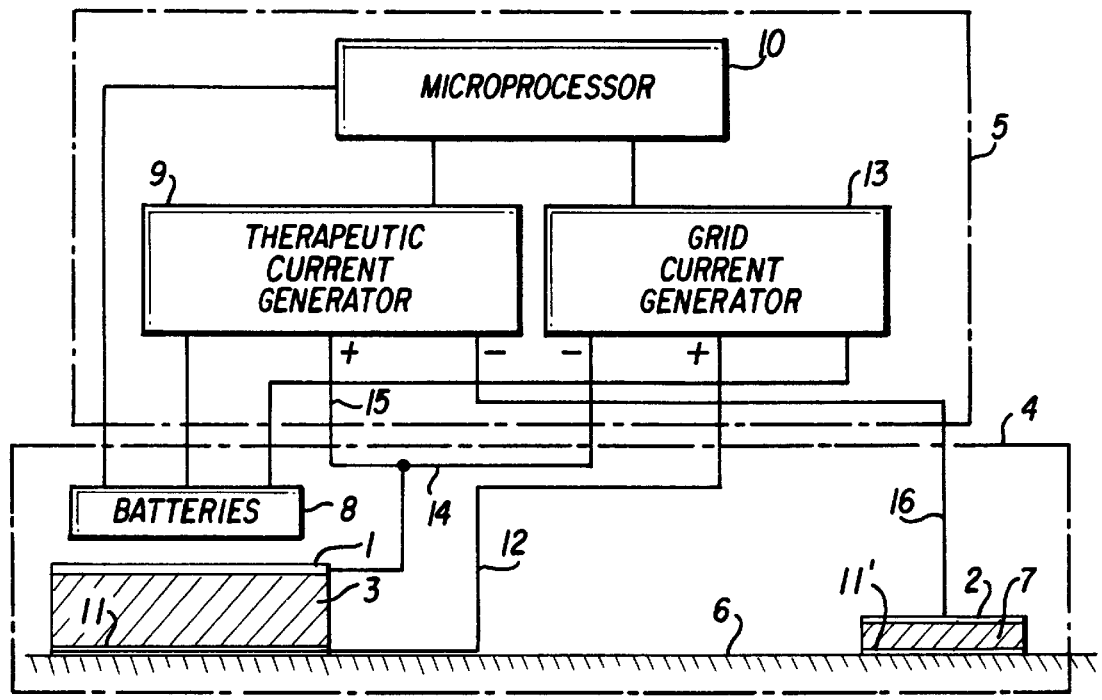

United States Patent [19]

Millot et al.

[11] Patent Number: 5,983,132
[45] Date of Patent: Nov. 9, 1999

[54] IONOPHORETIC DEVICE FOR TRANSDERMAL ADMINISTRATION OF MEDICAMENTS, AND DISPOSABLE ASSEMBLY FORMING PART OF SUCH DEVICE

[75] Inventors: Philippe Millot, Dijon; Eric Teillaud, Talant; Michel Lamoise, Bessey-les-Citeaux, all of France

[73] Assignee: Laboratoires d'Hygiene et de Dietetique (L.H.D.), Paris, France

[21] Appl. No.: 08/836,308

[22] PCT Filed: Nov. 16, 1995

[86] PCT No.: PCT/FR95/01509

§ 371 Date: May 12, 1997

§ 102(e) Date: May 12, 1997

[87] PCT Pub. No.: WO96/14896

PCT Pub. Date: May 23, 1996

[30] Foreign Application Priority Data

Nov. 16, 1994 [FR] France .................................. 94 13715

[51] Int. Cl.⁶ ................................ A61N 1/30; A61N 1/00
[52] U.S. Cl. .............................................. 604/20; 607/149
[58] Field of Search .................................. 604/20, 890.1; 607/149, 152

[56] References Cited

U.S. PATENT DOCUMENTS 5,006,108  4/1991  LaPrade ..................................... 604/20
5,013,293  5/1991  Sibalis ....................................... 604/20
5,246,417  9/1993  Haak et al. ................................. 604/20

FOREIGN PATENT DOCUMENTS

90/03825  4/1990  WIPO .
91/05582  5/1991  WIPO .
93/09842  5/1993  WIPO .
93/14813  8/1993  WIPO .

*Primary Examiner*—Ronald Stright
*Assistant Examiner*—Michael J. Hayes
*Attorney, Agent, or Firm*—Stevens, Davis, Miller & Mosher, L.L.P.

[57] ABSTRACT

The device comprises a reservoir (3) containing an active principle in ionized form, first (1) and second (2) electrodes in contact with a face of the reservoir (3) and the skin (6) of the patient, respectively, the other face of the reservoir being applied to the skin (6) of the patient and means (5) for circulating selectively an electric current between said electrodes in order to help the passage of a flow of active principle under the patient's skin. The device further comprises a) a control grid (11) arranged on the face of the reservoir (3) which is intended to be applied to the skin (6) of the patient and b) control means (10), (9), (13) for cutting off the assistance current during a predetermined period of time and to circulate a reverse current between the grid (11) and the first electrode (1) which is intended to cancel substantially the passive flow of ions of the active principle which would otherwise pass under the patient's skin.

9 Claims, 2 Drawing Sheets

IONOPHORETIC DEVICE FOR TRANSDERMAL ADMINISTRATION OF MEDICAMENTS, AND DISPOSABLE ASSEMBLY FORMING PART OF SUCH DEVICE

The present invention relates to an iontophoretic device for transdermal delivery of medicinal products and, more particularly, to such a device comprising a reservoir for an active principle in ionized form, having two substantially parallel faces, first and second electrodes in electrical contact with a face of the reservoir and the skin of the patient, respectively, the other face of the reservoir being intended to be applied onto a region of the skin of the patient which lies away from the region on which the second electrode bears, and means for selectively passing an electric current between these electrodes, in order to assist the passage of a flow of the active principle under the skin of the patient. The present invention also relates to a disposable assembly forming part of such a device.

FIG. 1 of the attached drawing diagrammatically represents an iontophoretic device for transdermal delivery of medicinal products comprising, in a known manner, first and second electrodes 1, 2 respectively, at least one of these electrodes (the first in the figure) being attached to a reservoir 3 for a solution containing an active principle in ionized form. By way of example, this reservoir 3 may consist of a layer of hydrogel impregnated with the solution of active principle.

The two electrodes and the reservoir may be incorporated in a disposable assembly 4 designed to be detachably combined with an electronic module 5. The device consisting of the disposable assembly and the electronic module is designed to be fixed on a limb of a patient so that the reservoir 3 is applied onto the skin 6 of this patient, like the electrode 2, on a region of the skin which is adjacent to the region which receives the reservoir. As represented, a layer 7 of a product for protecting the skin of the patient, such as an electrically conducting hydrogel, may be formed on the electrode 2 in order to be interposed between this electrode and the skin 6 of the patient.

The electronic module 5 is supplied with electrical energy by batteries 8, preferably placed inside the disposable assembly 4. These batteries thus supply a "therapeutic" current generator 9 and a microprocessor 10 programmed to control this generator.

During use of this device, the reservoir 3 of the assembly 4 is filled with the solution of active principle to be delivered, the assembly 4 is installed on the electronic module 5 and they are fixed on a limb of the patient, for example with the aid of a strap, so that the reservoir 3 and the hydrogel 7 are applied against the skin 6 of the patient. Supply of the generator 9 and of the microprocessor 10 by the batteries 8 is then activated so that this microprocessor causes an electric current to be set up between the electrodes 1, 2, under the skin of the patient, the polarity of the current being chosen so that the ions of the active principle pass under the skin of the patient, from the reservoir 3, by flowing down the electric field thus set up.

It will be understood that it is then possible to programme the microprocessor 10 so that it selectively controls the setting up of the current between the electrodes and the strength of this current. Thus, in a known manner, a current is caused, for example, to flow for one hour, then this current is cut off for the following two hours before subsequently being reapplied, etc. according to a time programme thus spreading over six hours or more. The cut-offs of the current are used, in particular, to ensure "depolarization" as well as physiological rest of the skin of the patient, so as to limit its denaturing, which denaturing causes detrimental effects to its characteristics of permeability to the active principle.

It is observed that, during the periods in which the "therapeutic" current is cut off, active principle continues to pass under the skin of the patient, without it being possible to control the "passive" flow of active principle which is then set up. This is an osmotic flow due to the concentration gradient of the active principle which is present at the interface between the reservoir and the skin of the patient, which gradient causes active principle to pass under the skin in a conventional transdermal device, without iontophoretic assistance. This absence of control with regard to passage of the active principle during the periods in which the therapeutic current is cut off is not without drawbacks, especially when the quantity of active principle to be delivered must be controlled very carefully, as is the case, for example, when this active principle is a powerful analgesic such as fentanyl or its derivatives, which may be dangerous in the event of exceeding the prescribed dosage.

International Patent Application WO 90/03825 discloses a membrane designed to be fitted in an iontophoretic device for transdermal delivery of medicinal products, this membrane substantially reducing the flow of active principle which passes under the skin of the patient during the periods in which the therapeutic current is cut off. In the long term, however, throughout the duration of a transdermal delivery of medicinal products, progressive denaturing of the skin of the patient is observed, which denaturing progressively increases its permeability to the active principle. With the membrane described in the aforementioned patent, no means is provided making it possible to correct this increase over time of the passive flow, by acting on the permeability of the said membrane.

The object of the present invention is to provide an iontophoretic device for transdermal delivery of medicinal products which is designed to reduce or stop passage of a passive flow of active principle during the periods for depolarizing the skin of the patient and for correcting for any drift in the permeability of the skin due to progressive denaturing.

These objects of the invention, as well as others which will appear in the rest of the description which is to follow, are achieved with an iontophoretic device for transdermal delivery of medicinal products, of the type described in the preamble of the present description, which is noteworthy in that it furthermore comprises a) a control grid made of electrically conducting material, arranged on the face of the reservoir intended to be applied onto the skin of the patient and b) control means for cutting the therapeutic current for a predetermined time interval and for then passing a current in the opposite direction between the grid and the first electrode, which current can reduce or substantially stop the passive flow of ions of the active principle which would then otherwise pass under the skin of the patient.

By virtue of the control grid of the device according to the invention, not only is it possible to control the passive flow of active principle when the therapeutic current is cut off, but it is also possible to correct the effects of possible denaturing of the skin of the patient during the treatment, as will be seen in the rest of the present description.

In a preferred embodiment of the device according to the invention, the control means set up an inverse current between the grid and the first electrode during a fraction of the predetermined time interval, starting from the beginning of this time interval. This thus facilitates resumption of the passage of the flow of the active principle at the end of the time interval during which this passage is inhibited, as will be seen hereinbelow.

Conveniently, the device according to the invention comprises a removable and disposable assembly consisting of the first and second electrodes, at least one reservoir attached to one electrode and capable of holding a solution of active principle, at least one control grid bonded to this reservoir and an electrical power source supplying the assistance current, the inverse current and the electrical supply of the means for controlling these currents.

Other characteristics and advantages of the present invention will emerge on reading the following description and on examining the attached drawing, in which:

FIG. 1 is a diagram of the device according to the invention, already partially described in the preamble of the present description.

Figure 2:
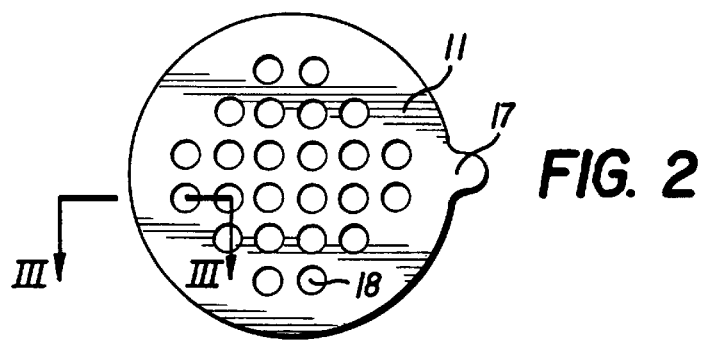
Figure 3:
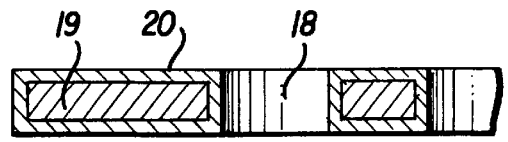
Figure 4:
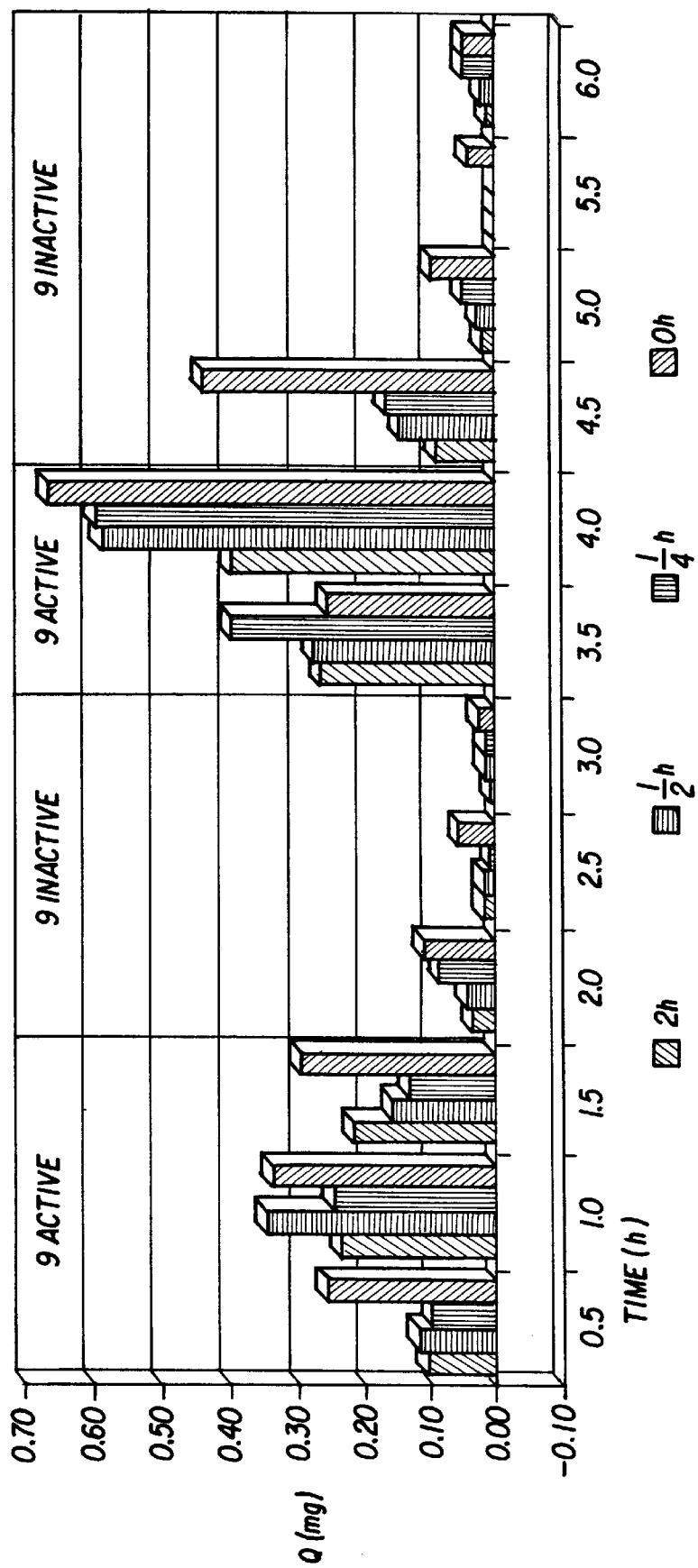

FIG. 2 is a plan view of a control grid incorporated with the device according to the invention, FIG. 3 is a diagrammatic, partial and enlarged sectional view of an embodiment of the grid in FIG. 2, taken along the section line III—III in this figure, and FIG. 4 is a time diagram of the flows of active principle observed in in vitro trials intended to measure the efficiency of the device according to the invention.

Returning to FIG. 1 of the attached drawing, it is shown that the device according to the invention comprises a control grid 11 placed against that face of the reservoir 3 which is intended to be applied against the skin 6 of a patient. The grid is made of an electrically conducting material. The skin of the patient is optionally protected from direct contact with this grid by a thin layer of a hydrogel such as that constituting the layer 7 plated against the second electrode 2.

The grid 11 is connected by a line 12 to a grid current generator 13 which is also connected to the first electrode by a second line 14. The microprocessor 10 constitutes means for selectively controlling the two generators 9, 13. Thus, this microprocessor is duly programmed in order to execute a programme for delivering the medicinal product contained in the reservoir 3, by controlling the passage of a current from a line 15 to a line 16, respectively connecting the first and second electrodes to the two outputs of the generator 9, via the subcutaneous part of the body of the patient contained between these electrodes, then by cutting this delivery by deactivating the generator 9, in particular during a predetermined time interval.

According to the present invention, the microprocessor 10 activates the generator 13 at the start of this predetermined time interval. A current whose direction is opposite that of the therapeutic current previously set up then flows between the control grid 11 and the first electrode 1.

It will be understood that, when the generator 9 is activated by the microprocessor 10, the grid 11 is not supplied with current. It therefore opposes passage of the active principle only by a mechanical screen effect which is minimized by a suitable open-worked structure. The transdermal delivery of medicinal products under iontophoretic assistance is therefore accomplished normally.

Conversely, when the microprocessor 10 activates the generator 13 and cuts off the generator 9, the grid 11 becomes an anode and the electrode 1 becomes a cathode. If the active principle contained in the reservoir is cationic, the cations which constitute it will then be directed towards the first electrode which has become a cathode. The flow of cations thus set up therefore opposes the "passive" flow of the cations of the active principle which is otherwise observed in conventional transdermal delivery, without iontophoretic assistance. By thus efficiently stopping or braking the flow of active principle during the time intervals of a delivery programme where it is desired to stop this flow, better "depolarization" of the skin of the patient, on the one hand, and, on the other hand, more rigorous control of the quantities of active principle actually delivered to this patient are ensured.

FIG. 2 represents a possible geometry for the control grid 11 to be attached to the reservoir 3 of active principle. This grid is pierced with regularly distributed openings 18 intended to ensure passage of a flow of activated principle ionotophoretically when the generator 9 delivers current between the electrodes 1 and 2. As seen hereinabove, the grid may be made from a thin film (having a thickness of 25 μm, for example) of a conducting metal such as silver, copper, zinc or gold.

The active principle is often introduced in a solution of sodium or potassium chloride, for example, and it is the solution which impregnates the reservoir 3. When the grid current generator 13 is activated, and if the grid (which is then the "anode") consists of simple metal, the $Cl^-$ ions of the solution are plated onto the grid, which causes depletion of the solution with respect to $Cl^-$ ions.

In order to avoid lowering of the conductivity of the reservoir and electrolysis of the water, which would increase the pH of the solution, resulting in irritation of the skin of the patient, it is preferable to use a control grid made of silver electrochemically plated with AgCl, which avoids consumption of the $Cl^-$ ions of the solution when the grid is supplied. FIG. 3 of the attached drawing represents an enlargement of the partial section, along the section line III—III in FIG. 2, showing an perforated silver sheet 19 covered with silver chloride plating 20. The first and second electrodes may moreover be constituted similarly.

The control grid 13 might also consist of an perforated polymer film covered with carbon or, using silk-screen printing, with a conductive ink.

The efficiency of the device according to the invention is illustrated by the time diagram in FIG. 4, established using "in vitro" measurement cells, each comprising a chamber for a medium holding ions of an active principle, in this case morphine hydrochloride, which are passed through a skin sample attached to the reservoir of the device in FIG. 1. The electrode 2 of this device is then soaked in the holding medium for ensuring flow of the electric current through the skin. By periodically determining the active principle concentration of the holding medium, it is possible to calculate the quantity Q (in mg) of active principle which has crossed the skin during a predetermined time interval, either under therapeutic current (generator 9 active) or during a rest period (generator 9 inactive).

The treatment programme illustrated by FIG. 4 lasts 6 hours and comprises two periods of delivering the medicinal product under therapeutic current, of 1 hour, each followed by a rest period (generator 9 inactive) of 2 hours. The direct currents delivered by the generators 9 and 13 are respectively 1 mA and 8 mA.

Advantageously, the generator 13 may comprise a cut-off supply capable of delivering this current of 8 mA, under 40 to 60 volts, for example, from the voltage of a few volts delivered by the batteries 8.

The influence of the duration of the supply of the control grid 11 of the device according to the invention, during the rest periods, was studied. Thus, the diagram in FIG. 4 gives the mean values of the measurements obtained with four groups of cells, the control grids of which were supplied by the generator 13 for two hours, ½ hour, ¼ and 0 hour, respectively, during the rest periods, starting from the beginning of these periods. The graph makes it possible to measure the efficiency of the control grid of the device according to the invention and the influence of the duration of its supply in the rest period.

A degree of dispersion in the quantities of active principle which have crossed the skin samples during the first hour under therapeutic current is observed even though the four groups of cells in question comprise skin samples which have not yet been subjected to a period of activation of the control grid 11. This dispersion is explained by the unavoidable dispersion in the characteristics of the skin samples placed in the cells. It is simply observed that the presence of the control grid, by virtue of its mechanical screen effect, tends to reduce the flow of active principle.

During the two hours following the end of this first time interval, of one hour, the therapeutic current is cut off and the grid 11 is supplied. A great reduction in the quantities of active principle which then cross the skin samples, in comparison with the quantity resulting from the "passive" flow alone (no supply of the grid 11) is observed. This proves the efficiency of the said grid in its role of blocking or reducing this passive flow. The present invention thus makes it possible to control more precisely the quantities of active principle transmitted to the patient, by reducing or by eliminating the influence of the "passive" flow during the necessary periods of resting the skin, in which the therapeutic current is suppressed. It is even possible, according to the invention, to reduce this passive flow in a controlled manner by varying, for example, the current delivered by the grid current generator 13 during the cut-off periods of the generator 9. The invention therefore offers constant control of the flow of active principle both under therapeutic current and in the absence of such a current.

On resumption of the therapeutic current (fourth hour of the treatment) it is observed that the quantities of active principle crossing the skin are greatly enhanced in comparison to those observed during the first hour. This is due to the denaturing of the skin due to the current and to the occlusive effect of the electrodes which have operated for the preceding three hours, which denaturing has the effect of increasing the permeability of the skin to the active principle, despite the moderation of this increase due to the intermediate depolarization period of two hours.

It is observed that resumption of passage of the active principle is commensurately greater as the duration of application of a blocking current to the grid 11 during the prior rest period is short. This observation can be used to accelerate or delay delivery of the total quantity of active principle necessary for the patient as a function of pharmacological considerations. During the rest period of two hours which follows the second application of the therapeutic current to the electrodes 1 and 2 by the generator 9, resupplying the control grid 11 further greatly reduces the passive flow of active principle through the skin, in comparison to that which is observed without supplying the control grid.

The trials described hereinabove were repeated by replacing the direct currents used by currents pulsed at the frequency of 500 Hz with a duty ratio of 50% in order to improve depolarization of the skin. The results observed as regards control of the passive flow of active principle are of the same order and confirm those obtained with direct current.

It thus appears that the invention indeed makes it possible to achieve the desired object, i.e. great reduction of the "passive" flow observed when the therapeutic current is cut off. Advantageously, the microprocessor 10 may be equipped with means for varying the duration of application of the current delivered by the generator 13 to the control grid, so as to allow action on the subsequent "resumption" of the flow of active principle, as was seen hereinabove.

The microprocessor 10 may also be equipped with means making it possible to vary the strength of the supply current of the control grid, so as advantageously to correct any drift over time in the permeability of the skin of the patient to the active principle.

Also advantageously, the device according to the invention may be equipped with means sensitive to the voltage set up between the first electrode 1 and the control grid 11 and to the strength of the current flowing between them for deducing therefrom a measure of the quantity of active principle remaining in the reservoir 3, according to the method described in the French patent application filed on May 6, 1994 by the Applicant Company and entitled "Method and device for measuring the quantity of active principle contained in a reservoir".

Clearly, the invention is not limited to the embodiment described and represented, which was given only by way of example. Thus, the device may comprise a second reservoir 7 of active principle and a second control grid 11 combined with the second electrode 2 for selectively establishing a flow of active principle from this second reservoir and for selectively blocking the inverse passive flow during a period of cutting off the assistance current passing from the second electrode to the first electrode, below the skin of the patient.

It was seen hereinabove that the control grid may consist of a metal which is identical to that of the electrodes 1 and 2. As a variant, another metal might be chosen for constituting the control grid, so as to establish an electrochemical couple between this grid and the electrode 1, which can reinforce blocking of the ions of the active principle during the rest period, without thereby substantially reducing the strength of the therapeutic current during the periods of delivery of the active principle.

Similarly, the invention is also applicable to a conventional transdermal device having no means for supplying a therapeutic assistance current. Its use is, however, particularly suitable in a device for transdermal delivery under iontophoretic assistance, by virtue of the presence of electrodes which are necessary for passage of the therapeutic current as well as for the inverse current according to the present invention.

The invention also extends to the delivery of the hydrochlorate or another salt of metoclopramide or of melatonin and, more generally, to the delivery of any active principle.

We claim:

1. An iontophoretic device for transdermal delivery of medicinal products, comprising:

a reservoir for an active principle in ionized form, having two substantially parallel faces, a first electrode in electrical contact with one of said faces of said reservoir, a second electrode for being in electrical contact with a first region of the skin of the patient, the other of said faces of said reservoir being a face for applying onto a second region of the skin of the patient which lies away from the first region, passing means for selectively passing an electric current between said electrodes in a first direction, to assist the passage of a flow of the active principle under the skin of the patient, and a control grid made of electrically conducting material, arranged on the face of said reservoir for applying onto the skin of the patient, wherein said passing means comprises control means for cutting the assistance current for a predetermined time interval and for then passing a current in a direction opposite said first direction between said grid and said first electrode, which current can reduce or substantially stop the passive flow of ions of the active principle which would then otherwise pass under the skin of the patient.

2. The device according to claim 1, wherein said control means establishes an inverse current between said grid and said first electrode for a fraction of the predetermined time interval, starting from the beginning of said time interval.

3. The device according to claim 2, wherein said control means comprise means for varying the duration of said fraction of the predetermined time interval and means for varying the strength of said inverse current then applied.

4. The device according to claim 1, further comprising means sensitive to the voltage set up between said first electrode and said control grid and to the strength of the current flowing between them for deducing therefrom a measure of the quantity of active principle remaining in the reservoir.

5. The device according to claim 1, further comprising a second reservoir of active principle and a second control grid associated with said second electrode for selectively establishing a flow of active principle from said second reservoir and for selectively blocking the passive flow in the cut-off period of an assistance current passing from said second electrode to the first electrode.

6. The device according to claim 1, wherein said control grid consists of a conductive metal.

7. The device according to claim 6, wherein said conducting metal is chosen to form an electrochemical couple with the metal constituting said first electrode, capable of reinforcing blocking of the ions of the active principle in the rest period.

8. The device according to claim 1, in which the active principle is introduced into the reservoir by means of a solution of NaCl, wherein said grid consists of metal silver plated with $Cl^-$ ions.

9. Device according to claim 1, wherein said grid consists of a perforated film of a polymer material, covered with a conductive material.

* * * * *